United States Patent
Mann

(10) Patent No.: US 6,699,514 B2
(45) Date of Patent: Mar. 2, 2004

(54) MICROORGANISMS AND THEIR USE IN ANIMAL FEED

(75) Inventor: Stephen Philip Mann, Cambridge (GB)

(73) Assignee: Biotal Ltd. (GB)

( * ) Notice: Subject to any disclaimer, the term of this patent is extended or adjusted under 35 U.S.C. 154(b) by 0 days.

(21) Appl. No.: 09/767,355

(22) Filed: Jan. 23, 2001

(65) Prior Publication Data

US 2001/0055633 A1 Dec. 27, 2001

Related U.S. Application Data

(63) Continuation-in-part of application No. 09/637,459, filed on Aug. 11, 2000, now Pat. No. 6,326,037, which is a continuation-in-part of application No. 09/125,212, filed as application No. PCT/GB97/00433 on Feb. 17, 1997.
(60) Provisional application No. 60/016,988, filed on May 7, 1996.

(30) Foreign Application Priority Data

Feb. 15, 1996 (GB) ............................................... 9603168

(51) Int. Cl.$^7$ ................................................. A23K 1/00
(52) U.S. Cl. ............................... 426/2; 426/54; 426/53
(58) Field of Search ................................ 426/2, 52, 53, 426/54, 61, 623, 635, 636; 424/93.45

(56) References Cited

U.S. PATENT DOCUMENTS

| | | | |
|---|---|---|---|
| 4,160,038 A | | 7/1979 | Groben et al. |
| 4,264,448 A | * | 4/1981 | Bodenrader .................. 210/611 |
| 4,842,871 A | | 6/1989 | Hill |
| 5,747,020 A | | 5/1998 | Rutherford et al. |
| 5,811,289 A | * | 9/1998 | Lewandowski et al. ..... 435/262 |

FOREIGN PATENT DOCUMENTS

| | | |
|---|---|---|
| EP | 0311469 | 4/1989 |
| EP | 0322569 | 4/1989 |
| EP | 0408220 | 1/1991 |
| EP | 0580236 | 1/1994 |
| JP | 5084066 | 4/1993 |
| SU | 1777772 | 11/1992 |
| WO | 8002282 | 10/1980 |

OTHER PUBLICATIONS

Cooke, L. [1995] "New Strain Slows Silage Spoilage," *Agricultural Research*, Jun. 1995, 43(6): 17.
Dellaglio, F., et al. [1996] "DNA–DNA Homology, Physiological Characteristics and Distribution of Lactic Acid Bacteria Isolated from Maize Silage." *Journal of Applied Bacteriology*, 60 (2):83–92.
Driehuis, F., et al. [1996] "Improving Aerobic Stability by Innoculation with *Lactobacillus buchneri*," *Proceedings of the 11$^{th}$ International Silage Conference*, 106–107.
Muck, R.E. [1996] "A Lactic Acid Bacterial Strain to Improve Aerobic Stability of Silages." *Research Summaries of the U.S. Dairy Forage Research Center*, 46–47.
Seale, D.R., et al. [1985] "Effect of Innoculation with Homofermentative and Heterofermentative Lactic Acid Bacteria on Silage Fermentation," The Edinburgh School of Agriculture, U.K.
Weinberg, Z.G., et al. [1996] "New Trends and Opportunities in the Development and Use of Innoculants for Silage," *FEMS Microbiology Reviews*, 19:53–68.
Patent Abstracts of Japan, [1993] 17(409), C–1091 & JP 05 084066 A (Asahi Breweries LTD) [1993] (abstract).
Database WPI, Section Ch, Week 9349, Derwent Publications Ltd., London, GB; Class D13, AN 93–393864, XP002034344 & SU 1 777 7772 A (Kaluga Sect Mosc Agric Acad), [1992] (abstract).

* cited by examiner

*Primary Examiner*—Keith Hendricks
(74) *Attorney, Agent, or Firm*—Saliwanchik, Lloyd & Saliwanchik

(57) ABSTRACT

A method for treating an animal selected from the group consisting of pigs, poultry and ruminants, to increase the animal's performance, which comprises administering to the animal, with its feed, a performance-increasing amount of an organism selected from the group consisting of *Lactobacillus buchneri, Lactobacillus kefir, Lactobacillus parakefir* and *Lactobacillus parabuchneri*.

18 Claims, No Drawings

MICROORGANISMS AND THEIR USE IN ANIMAL FEED

CROSS-REFERENCE TO RELATED APPLICATIONS

This is a continuation-in-part of application Ser. No. 09/637,459, filed Aug. 11, 2000, now U.S. Pat. No. 6,326,037 which is a continuation of copending application Ser. No. 09/125,212, filed Mar. 22, 1999, which is a national stage application of International Patent Application No. PCT/GB97/00433, filed Feb. 17, 1997, which claims priority from provisional Application Ser. No. 60/016,988, filed May 7, 1996.

FIELD OF THE INVENTION

This invention relates to micro-organisms and their use in animal feed.

BACKGROUND OF THE INVENTION

The use of enzymes and organisms can improve or enhance the performance of animals and the value of the feed the animals receive. For example, WO-A-9210945 discloses such a combination for use in enhancing the value of prepared silage. WO-A-9313786 and WO-A-9617525 relate to enhancement of animal performance using microorganisms; WO-A-93/3786 refers to species of Lactobacillus.

It is a common practice in the rearing of beef cattle for the animals to be 'finished' on a feedlot for a period of around 140 days prior to slaughter. The aim of the finishing process is to produce beef in a form most acceptable to the consumer. During finishing, there is an increase in muscle (red meat) mass as well as an increase in the amount of fat. Whilst in the feedlot, the animals are switched to a diet which is high in energy and low in fibre, commonly known as 'concentrates', mostly cereal grains and especially corn (*maize*). The switch to high levels of carbohydrate-containing feeds can lead to a number of problems, including bloat, acidosis and various ruminal toxicosis symptoms. These conditions can be detrimental to the health of the animal and, in severe cases, can be fatal.

Since the 1980's, direct fed microbials (DFMs) have been utilised in cattle feedlot rations. These include a number of strains of bacteria, fungi and yeast. During the first 10 years of the use of DFMs, *Lactobacillus acidophilus* was one of the most commonly utilised microbial feed additives. When feeding *Lactobacillus acidophilus*, the most accepted mode of action is competitive exclusion in the lower gut. That is, *Lactobacillus acidophilus* will out-compete harmful or pathogenic bacteria for attachment sites on the intestinal wall.

More recently, Propionibacteria such as *Propionibacterium freudenreichii* have become widely used as a DFM for feedlot cattle. When *Propionibacterium freudenreichii* is fed in high grain diets to cattle, ruminal lactate levels are reduced by conversion of the lactate to propionate. Thus the severity of ruminal acidosis is reduced.

Strains of the micro-organism Bacillus have also been shown to be beneficial in finishing cattle. In this case, the mode of action is thought to be oxygen-scavenging. Many of the specialist fibre-degrading organisms in the rumen are obligate anaerobes, and, during the process of chewing and swallowing, dissolved oxygen can be introduced into the rumen. This will have a negative effect on the rumen microbes. Bacillus strains have a preference for this oxygen, and will grow very quickly utilising the available oxygen and re-establishing the anaerobic conditions.

SUMMARY OF THE INVENTION

It has now been found that *Lactobacillus buchneri* and related organisms are suitable for use as a direct fed microbial, and has a mode of action distinct from those described above, i.e. the conversion of dietary carbohydrate to acetic acid. It may therefore be used to increase an animal's performance.

When feeding *L. buchneri* in high grain diets, in accordance with the present invention, greater amounts of carbohydrate can be converted to acetic acid on a net basis. This has the effect of buffering the rumen and reducing the effects of acidosis.

There are also secondary advantages in the conversion of carbohydrate to acetate rather than propionate. Prior to arriving at the feedyard, cattle are fed a forage-based diet, and during this time period, the energy consumed is about 1.5 times maintenance. During forage feeding, the ruminal concentration of acetic acid to propionic acid is 3:1 or higher. When shifted onto the high concentrate diet, energy consumption is about 3 times maintenance, and the ruminal ratio of acetic acid to propionic acid is reduced from 3:1 to 1:1. Thus, the ruminal fermentation of propionate may be up to six times higher than previously. As the eventual fate of propionate is conversion to glucose in the liver, and the glucose requirement by a finishing steer is relatively low, it may be that this adaptation, to propionate metabolism, is rate-limiting to growth performance in feedlot cattle.

With high grain feeding, the inclusion of *L. buchneri* in the total mixed ration will result in similar energy intake, with a greater amount of acetic acid to be used for metabolic purposes and thus improved animal performance. Improved performance may be evident as, for example, increased weight gain and/or improved feed efficiency.

DESCRIPTION OF THE INVENTION

An organism of the species *Lactobacillus buchneri*, that is suitable for use in this invention, has been deposited at the National Collection of Industrial and Marine Bacteria on Feb. 13, 1996. Its accession number is 40788.

The subject culture has been deposited under conditions that assure that access to the culture will be available during the pendency of this Patent Application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit is stored and made available to the public in accord with the provisions of the Budapest Treaty for the Deposit of Microorganisms, i.e. it is stored with all the care necessary to keep it viable and uncontaminated for a period of at least five years after the most recent request for the furnishing of a sample of a deposit, and in any case, for a period of at least thirty (30) years after the date of deposit or for the enforceable life of any patent which may issue disclosing a culture. The depositor acknowledges the duty to replace a deposit should the depository be unable to furnish a sample when requested, due to the condition of a deposit. All restrictions on the availability to the public of the subject culture deposit will be irrevocably removed upon the granting of a patent disclosing it.

This organism has a surprising effect, different from and/or extending beyond that due to its ability to produce volatile fatty acids, such as acetic, propionic and lactic acids, that are normally produced in fermentation. The organism produces an antimicrobial substance or effect characterised by its ability to inhibit the growth of a variety of undesirable organisms, and which is stable at 80° C. but inactivated at 120° C. It is reasonable to assume that any such substance may be produced by other organisms, and such other organisms can be determined by screening, as is well known to those of ordinary skill in the art.

The antimicrobial substance or effect has been shown to have an influence on the microbial breakdown processes that occur within the rumen. When incubated in vitro with rumen fluid, animal feeds that have been treated with *Lactobacillus buchneri* show both a reduced rate of carbohydrate degradation and an increase in the lag time before structural fibre degradation occurs. Both these actions have a benefit in prevention of acidosis, in that as the carbohydrate and fibre degradation is slower, the potential for a peak of lactic acid following feeding is also reduced.

The activity associated with this invention may be found in other strains of *L. buchneri*, in other species of Lactobacillus, e.g. *L. kefir, L. parakefir* and *L. parabuchneri*, and possibly also in other genera. This can be established by routine experimentation, on the basis of the information herein.

The invention may be used with any animal feed, whether solid or liquid, e.g. for pigs, poultry or ruminants. Ruminants include but are not limited to beef cattle, dairy cattle, sheep, goats, bison, elk, deer and the like.

The feedstuff that is used may be conventional. It will be appreciated by those in the art that a suitable feedstuff depends on several factors, including the animals to be fed and also the locality. The ration fed usually contains forage, cereal grain, byproducts or a mixture thereof. Forages include various grasses, legumes and crop residues. Such forages may be processed or presented as whole, chopped, ground and/or ensiled. Cereal grains include corn, sorghun, wheat, rye, barley, oats and rice. Cereal grains are typically processed or presented as whole, cracked, ground, high moisture, ensiled or steam-flaked. Byproducts include those from fermentation of grain (such as, for example, corn, bran, distillers' grains, steep liquor), cotton processing (gin trash, cottonseed), milk processing (liquid whey), and a variety of others that may result from processing food for human consumption (potato waste, citrus pulp, almond hulls, peanut hulls, bakery waste, wheat midds).

An effective amount of the organism can readily be determined by the ordinarily skilled person. It will take into account the usual factors, such as the type, condition, age and weight of the animal. A typical daily dosage for cattle is between $10^5$ and $10^{14}$, e.g. $10^9$–$10^{10}$, CFU (colony forming units) per head per day.

The following Example illustrates the invention.

EXAMPLE

One hundred and ten steers were blocked by weight into two groups (42 steers at 982 pounds, 68 steers at 834 pounds). Within the block of heavier steers, cattle were stratified by weight and randomly allotted to six pens, resulting in six pens with seven head per pen. Within the block of lighter steers, cattle were stratified by weight and randomly assigned to 10 pens, resulting in 8 pens with seven head and two pens with six head per pen. Within the blocks, two dietary treatments were randomly allotted to pens of cattle. Treatments consisted of no microbial feed additive (control) or *L. buchneri* added to the total mixed ration at a rate of $10^9$ colony-forming units per head per day. Freeze-dried cells of *Lactobacillus buchneri* were dissolved in tap water and poured onto the mixing feed.

Cattle were fed once daily at approximately 09:00. The goal was, not only to obtain a 'slick' bunk just before feeding, but also that the cattle should approach the feed bunk in a non-aggressive manner at feeding time. To minimize cross-contamination of the microbial feed additive, a separate feed truck was used for each diet.

Cattle were adapted to their final diets in 20 days using three step-up diets. The final diet contained (DM basis) 15% corn silage, 77% steam flaked corn, 5% soybean meal and 3% mineral supplement. Diet nutrition formulation, dietary Rumensin and Tylan (feed antibiotics) levels and cattle management (implants, vaccination, parasite control) were typical for finishing cattle in the High Plains area.

Initial weight was based on the average of two consecutive daily weights and final weight on one daily weight. The heavy block of steers (42 head) was fed for 112 days and the light block of steers (68 head) was fed for 140 days. Pen means were generated and data analyzed as a randomised complete block design. The results are shown in the following Table.

TABLE

|  | Control | L. buchneri | SE | P-value |
|---|---|---|---|---|
| Number of pens | 8 | 8 |  |  |
| Number of steers | 55 | 55 |  |  |
| Initial weight (lb) | 910 | 907 | 4.09 | .5761 |
| Final weight (lb) | 1344 | 1366 | 8.84 | .0874 |
| DM feed intake (lb/d) | 19.20 | 19.45 | .28 | .5295 |
| Daily gain (lb) | 3.47 | 3.67 | .06 | .0184 |
| Feed/gain | 5.56 | 5.32 | .10 | .0790 |
| Ruminal acetate: propionate ratio | 1.16 | 1.32 |  |  |

The results in the Table show that, compared to control, steers fed the diet containing *L. buchneri* gained 5.8% faster (P=0.02), were 4.3% more efficient (P=0.09) and were 22 pounds heavier (P=0.09) at the end of the feeding period.

Analysis of volatile fatty acids in the rumen showed a higher acetate:propionate ratio in the cattle fed *L. buchneri*, supporting the proposed mode of action of *L. buchneri* in terms of conversion of ruminal carbohydrate into acetate.

What is claimed is:

1. A method of increasing the feed efficiency of animals comprising:
   a) administering, to said animals, multiple feedings of a solid feed comprising:
      i) forage, cereal grains, byproducts, or mixtures thereof; and
      ii) an amount of an organism that increases the feed efficiency of said animals;
   wherein: a) said organism is selected from the group consisting of *Lactobacillus buchneri, Lactobacillus kefir, Lactobacillus parakefir* and Lactobacillus parabuchneri; b) said amount of organism has been added to the solid feed; and c) said byproducts are cottonseed, gin trash, cotton processing byproducts, potato waste, citrus pulp, almond hulls, corn, bran, distillers' grains, peanut hulls, bakery waste, wheat midds, or mixtures thereof.

2. The method according to claim 1, wherein said organism is *Lactobacillus buchneri*.

3. The method according to claim 1, wherein said animals are selected from the group consisting of pigs, poultry, and ruminants.

4. The method according to claim 3, wherein said animals are pigs.

5. The method according to claim 3, wherein said animals are poultry.

6. The method according to claim 3, wherein said animals are ruminants.

7. The method according to claim 6, wherein said ruminants are cattle.

8. The method according to claim 1, wherein the solid feed contains an amount of organism that provides between $10^5$ and $10^{14}$ colony forming units (CFU) per animal per day.

9. The method according to claim 1, wherein the solid feed contains an amount of organism that provides between $10^9$ and $10^{10}$ colony forming units (CFU) per animal per day.

10. The method according to claim 1, wherein said forage comprises grasses, legumes, or crop residue; said cereal grain is corn, sorghum, wheat, rye, barley, oats, or rice; or mixtures thereof.

11. The method according to claim 10, wherein said forage or cereal grain is whole, chopped, ground, ensiled, cracked, high moisture, or steam-flaked.

12. A method of increasing the feed efficiency of ruminants comprising:
    a) administering, to said ruminants, multiple feedings of a solid feed comprising:
        i) forage, cereal grains, byproducts, or mixtures thereof; and
        ii) an added amount of an organism that increases the feed efficiency of said animals that is selected from the group consisting of *Lactobacillus buchneri, Lactobacillus kefir, Lactobacillus parakefir* and *Lactobacillus parabuchneri*;

wherein said byproducts are cottonseed, gin trash, cotton processing byproducts, potato waste, citrus pulp, almond hulls, corn, bran, distillers' grains, peanut hulls, bakery waste, wheat midds or mixtures thereof.

13. The method according to claim 12, wherein said organism is *Lactobacillus buchneri*.

14. The method according to claim 12, wherein said ruminants are cattle.

15. The method according to claim 12, wherein the solid feed contains an added amount of organism that provides between $10^5$ and $10^{14}$ colony forming units (CPU) per animal per day.

16. The method according to claim 12, wherein the solid feed contains an added amount of organism that provides between $10^9$ and $10^{10}$ colony forming units (CPU) per animal per day.

17. The method according to claim 12, wherein said forage comprises grasses, legumes, or crop residue; said cereal grain is corn, sorghum, wheat, rye, barley, oats, or rice; or mixtures thereof.

18. The method according to claim 17, wherein said forage or cereal grain is whole, chopped, ground, ensiled, cracked, high moisture, or steam-flaked.

* * * * *